(12) United States Patent
Kavsak et al.

(10) Patent No.: US 12,360,115 B2
(45) Date of Patent: Jul. 15, 2025

(54) METHOD OF DETERMINING RISK OF AN ADVERSE CARDIAC EVENT

(71) Applicant: McMaster University, Hamilton (CA)

(72) Inventors: Peter Kavsak, Burlington (CA); Andrew Worster, Cambridge (CA)

(73) Assignee: McMaster University, Ontario (CA)

( * ) Notice: Subject to any disclaimer, the term of this patent is extended or adjusted under 35 U.S.C. 154(b) by 1245 days.

(21) Appl. No.: 15/756,274

(22) PCT Filed: Aug. 26, 2016

(86) PCT No.: PCT/CA2016/051011
§ 371 (c)(1),
(2) Date: Feb. 28, 2018

(87) PCT Pub. No.: WO2017/035639
PCT Pub. Date: Mar. 9, 2017

(65) Prior Publication Data
US 2018/0252724 A1 Sep. 6, 2018

Related U.S. Application Data

(60) Provisional application No. 62/211,074, filed on Aug. 28, 2015.

(51) Int. Cl.
| | |
|---|---|
| *G01N 33/66* | (2006.01) |
| *G01N 33/68* | (2006.01) |
| *G01N 33/70* | (2006.01) |
| *G01N 33/72* | (2006.01) |
| *G01N 33/80* | (2006.01) |
| *G01N 33/92* | (2006.01) |

(52) U.S. Cl.
CPC ......... *G01N 33/66* (2013.01); *G01N 33/6887* (2013.01); *G01N 33/70* (2013.01); *G01N 33/723* (2013.01); *G01N 33/80* (2013.01); *G01N 33/92* (2013.01); *G01N 2333/4712* (2013.01); *G01N 2333/58* (2013.01); *G01N 2333/8139* (2013.01); *G01N 2800/32* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | |
|---|---|---|
| 2011/0053179 A1 | 3/2011 | Datwyler et al. |
| 2011/0053191 A1 | 3/2011 | Hess et al. |
| 2014/0058743 A1 | 2/2014 | Snider et al. |
| 2014/0170694 A1 | 6/2014 | Vandersleen et al. |

FOREIGN PATENT DOCUMENTS

| | | | |
|---|---|---|---|
| EP | 1884777 | 2/2008 | |
| EP | 1884777 A1 * | 2/2008 | ......... G01N 33/6863 |
| WO | 2009064240 A1 | 5/2009 | |

OTHER PUBLICATIONS

Chan et al. (BMC Medicine vol. 8:11 pages) (Year: 2010).*
Karki et al. Indian Heart Journal vol. 67:529-537 (Year: 2015).*
International Search Report dated Mar. 9, 2017—PCT/CA2016/051011.
Hong et al., "GDF15 is a novel biomarker for impaired fasting glucose". Diabetes and Metabolism Journal, Dec. 2014 (Dec. 2014), vol. 36(6), pp. 472-479.
Cengiz et al., "Placental growth factor as a new marker for predicting abnormal challenge test results". Gynecological Endocrinology, Jul. 10, 2013 (Jul. 10, 2013), vol. 29(10), pp. 909-911.
Damman et al., "Multiple biomarkers at admission significantly improve the prediction of mortality in patients undergoing primary percutaneous coronary intervention for ST-segment elevation myocardial infarction". Journal of the American College of Cardiology, Dec. 28, 2010 (Dec. 28, 2010), vol. 57(1), pp. 29-36.
Almeida et al., "The value of NT-proBNP in early risk stratification of acute coronary syndromes". Revista Portuguesa de Cardiologia, 2006, vol. 25(1), pp. 71-75.
Beattie et al., "Perioperative cardiac biomarkers: the utility and timing". Current Opinion in Critical Care, Aug. 2013 (Aug. 2013), vol. 19(4), pp. 334-341.
Extended European Search Report dated Apr. 3, 2019—EP16840458.
Brown Jeremiah R et al: "Using biomarkers to improve the preoperative prediction of death in coronary artery bypass graft patients", Journal of American Society of Extra-Corporeal Techno, American Society of Extra-Corporeal Technology, Reston, VA, US, vol. 42, No. 4, Dec. 1, 2010 (Dec. 1, 2010), pp. 293-300.
Shortt, C. et al., "An approach to rule-out an acute cardiovascular event or death in emergency department patients using outcome-based cutoffs for high-sensitivity cardiac troponin assays and glucose". Clinical Biochemistry, Mar. 3, 2015 (Mar. 3, 2015), vol. 48(4-5): 282-287.
International Search Report of PCT/CA2016/051011 dated Nov. 10, 2016.
Written Opinion of PCT/CA2016/051011 dated Nov. 10, 2016.
Shortt, C. et al., Clinical Biochemistry, Mar. 3, 2015 (Mar. 3, 2015), vol. 48(4-5), pp. 282-287.
Hong et al., Diabetes and Metabolism Journal, Dec. 2014 (Dec. 2014), vol. 36(6), pp. 472-479.

(Continued)

*Primary Examiner* — Lori A. Clow
(74) *Attorney, Agent, or Firm* — Gowling WLG (Canada) LLP

(57) ABSTRACT

Methods of determining the risk of an adverse cardiovascular event or death in a mammal are provided which include determining in a biological sample obtained from the mammal the level of a combination of biomarkers selected from a glucose metabolism biomarker, a heart function biomarker, a renal function biomarker and at least one biomarker of cardiac injury. A score is allotted based on the level of each biomarker, and the cumulative score is indicative of the risk of an adverse cardiovascular event.

12 Claims, No Drawings

(56) References Cited

OTHER PUBLICATIONS

Cengiz et al., Gynecological Endocrinology, Jul. 10, 2013 (Jul. 10, 2013), vol. 29(10), pp. 909-911.
Damman et al., Journal of the American College of Cardiology, Dec. 28, 2010 (Dec. 28, 2010), vol. 57(1), pp. 29-36.
Almeida et al., Revista Portuguese de Cardiologia, 2006 vol. 25(1), pp. 71-75.
Beattie et al., Current Opinion in Critical Care, Aug. 2013 (Aug. 2013), vol. 19(4), pp. 334-341.

* cited by examiner

METHOD OF DETERMINING RISK OF AN ADVERSE CARDIAC EVENT

FIELD OF INVENTION

The present invention relates to a prognostic method in the field of cardiology, and in particular, to a laboratory score for use to confirm or rule-out an acute cardiovascular event in a patient, as well as for risk stratification (i.e. to identify risk in a patient for subsequent cardiovascular events).

BACKGROUND OF THE INVENTION

The optimum laboratory test to identify myocardial injury is cardiac troponin. For those patients presenting with chest pain to the emergency department (ED), a physician's decision to discharge a patient from the hospital or admit and treat them for myocardial infarction (MI or heart attack) is often based on the patient's cardiac troponin measurement. However, individuals may have detectable and elevated cardiac troponin measurements for several reasons other than due to MI. Thus, a laboratory test or laboratory score consisting of several biomarkers is needed to identify patients both in the ED and in the non-acute setting who are at risk of MI or another serious cardiac event (e.g. cardiac ischemia, heart failure, percutaneous coronary intervention (PCI), coronary artery bypass graft (CABG), or death) within days to months. In short, a method providing a laboratory score to identify those at lowest risk for a subsequent cardiac event or death would be a tremendous tool for ED physicians wishing to discharge patients following receipt of results of a first blood collection. This would save considerable time and money in that patients with low risk of a cardiac event could be discharged immediately, as opposed to waiting the recommended 3-6 hours in the ED before being discharged. Moreover, cardiac injury and risk for subsequent cardiac events are now being tested in the community population, as well as in other patient populations at risk for cardiac injury (e.g., cancer patients). A laboratory score method would also be helpful in guiding the care and management of these patients.

Thus, it would be desirable to develop an accurate method, such as a method that yields a laboratory score for use in the risk stratification of patients with possible cardiac injury.

SUMMARY OF THE INVENTION

The present invention provides methods useful to determine if a mammal is at a low or high risk for an adverse cardiac event and/or death when they present with a possible cardiac injury. Briefly, methods are provided in which various parameters can be measured in a biological sample from the mammal, e.g. blood, plasma or serum sample, to assess the risk of an adverse cardiac event.

In one aspect, a method of determining the risk of an adverse cardiac event in a mammal is provided comprising the steps of:
i) determining in a biological sample obtained from the mammal the concentration of a glucose metabolism biomarker, and allotting a score of 1 when the concentration is greater than a normal level of the glucose metabolism marker;
ii) determining in the biological sample the level of a heart function biomarker, and allotting a score of 1 when the level is greater than a normal level of the heart function biomarker, or determining in the biological sample the level of a renal function biomarker and allotting a score of 1 when the estimated glomerular filtration rate (eGFR) which is based on the level of the renal function biomarker is less than the normal level of eGFR;
iii) determining in the biological sample the level of at least one biomarker of cardiac injury using a high sensitivity assay, and allotting a score of 1 if the level is greater than the level of an ambulatory population at risk for future cardiovascular events but less than the level at which analytical variation occurs, allotting a score of 2 if the level is greater than the level at which analytical variation occurs and less than the upper limit of normal of a general population, and allotting a score of 3 if the level is greater than the upper limit of normal of the general population;
iv) generating a total laboratory score based on the sum of the scores for each of the biomarkers of i), ii) and iii), wherein a laboratory score of greater than 4 indicates a risk of an adverse cardiac event in the mammal with a likelihood ratio of greater than 1; and
v) administering a treatment of the adverse cardiac event to the diagnosed mammal when there is a laboratory score of greater than 4.

In another aspect, a method of determining the risk of an adverse cardiac event in a patient is provided comprising the steps of:
i) determining in a biological sample obtained from the mammal the concentration of a glucose metabolism biomarker, and allotting a score of 1 when the concentration is greater than a normal level of the glucose metabolism marker;
ii) determining in the biological sample the level of a heart function biomarker, and allotting a score of 1 when the level is greater than a normal level of the heart function biomarker;
iii) determining in the biological sample the level of a renal function biomarker and allotting a score of 1 when the estimated glomerular filtration rate (eGFR) which is based on the level of the renal function biomarker is less than the normal level of eGFR;
iv) determining in the biological sample the level of at least one biomarker of cardiac injury using a sensitive assay, and allotting a score of 1 if the level is at about the limit of detection of the biomarker, a score of 2 is allotted if the biomarker level is greater than the limit of detection but less than the upper limit of normal of the biomarker level in a general population and a score of 3 is allotted when the biomarker level is greater than the upper limit of normal of the general population;
v) generating a total laboratory score based on the sum of the scores for each of the biomarkers of i), ii) and iii), wherein a laboratory score of greater than 5 indicates a risk of an adverse cardiac event in the mammal with a likelihood ratio of greater than 1; and
vi) administering a treatment of the adverse cardiac event to the diagnosed mammal when there is a laboratory score of greater than 5.

In another aspect, a method of determining the risk of an adverse cardiovascular event or death in a mammal is provided comprising the steps of:
i) determining in a biological sample obtained from the mammal the concentration of a glucose metabolism biomarker, and allotting a score of 1 when the concentration is greater than a normal level of the glucose metabolism marker;
ii) determining in the biological sample the level of a renal function biomarker and allotting a score of 1 when the estimated glomerular filtration rate (eGFR) which is based on the level of the renal function biomarker is less than the normal level of eGFR;

iii) determining in the biological sample the level of at least two biomarkers of cardiac injury using a sensitivity assay, and allotting a score of 1 if the level is at about the limit of detection of the biomarker, a score of 2 is allotted if the biomarker level is greater than the limit of detection but less than the upper limit of normal of the biomarker level in a general population and a score of 3 is allotted when the biomarker level is greater than the upper limit of normal of the general population;

iv) generating a total laboratory score based on the sum of the scores for each of the biomarkers of i), ii) and iii), wherein a laboratory score of greater than 7 indicates a risk of an adverse cardiac event in the mammal with a likelihood ratio of greater than 1; and v) administering a treatment of the adverse cardiac event to the diagnosed mammal when there is a laboratory score of greater than 7.

In a further aspect, a kit for use in a method of determining the risk of an adverse cardiovascular event or death in a mammal is provided comprising a biomarker-specific reactant for one or more biomarkers selected from the group consisting of a glucose metabolism biomarker, a heart function biomarker, a renal function biomarker, and a cardiac injury biomarker, wherein the reactant is suitable for use to determine the level of the biomarker in a biological sample from the mammal, and guidelines indicating a score to be allotted based on the level of each target biomarker and indicating the relationship between a total score and risk of an adverse cardiovascular event.

These and other aspects of the invention will become apparent in the detailed description that follows by reference to non-limiting examples.

DETAILED DESCRIPTION OF THE INVENTION

A method for determining the risk of an acute or adverse cardiovascular event or death in a mammal based on the determination of the concentration or level of a combination of parameters, including parameters of cardiac injury such as cardiac troponin I and T, metabolism, e.g. glucose and related metabolites, renal function and heart function or hematology is provided. A laboratory score is allotted to each parameter based on the level of each of the parameters. The combined laboratory score is effective to determine if a patient is at risk of an acute or adverse cardiovascular event (e.g. myocardial infarction, cardiac ischemia, heart failure, percutaneous coronary intervention (PCI), coronary artery bypass graft (CABG)), or death, including identifying that a patient is at low risk of a cardiovascular event or death and can be ruled-out for further treatment, and/or identifying a patient at high risk and ruled-in for further medical treatment and management.

The first step of the method is to obtain a biological sample from a mammal to assess risk for myocardial injury, e.g. mammals with symptoms of chest pain would be a reasonable group to test. The term "biological sample" is meant to encompass any mammalian sample that may contain glucose, RDW, creatinine, cardiac troponin, e.g. troponin T and troponin I, and related proteins. Suitable biological samples include, for example, blood, serum, plasma, urine and cerebrospinal fluid. The sample is obtained from the mammal in a manner well-established in the art.

The term "mammal" is used herein to refer to both human and non-human mammals.

Once a suitable biological sample is obtained, it is analyzed for the level or concentration of each of the selected parameters or biomarkers, including a combination of biomarkers selected from a metabolic biomarker, e.g. glucose, or a biomarker that reflects glucose metabolism such as glycated hemoglobin A1c (HbA1c); a biomarker that provides prognostic information related to heart function such as red cell distribution width (RDW), natriuretic peptides such as brain natriuretic peptide (BNP) and amino-terminal pro-brain natriuretic peptide (NT-proBNP); a biomarker associated with renal function such as creatinine or cystatin c; and at least one biomarker indicative of cardiac injury, such as cardiac troponin, e.g. troponin T and/or troponin I, or other heart specific proteins such as heart-specific fatty acid binding protein. An amount of <1 mL of biological sample is generally used to conduct the determination of these biomarkers.

Methods used to determine the level or concentration of the biomarkers will exhibit an appropriate specificity for detection of the selected biomarker. Detection methods may vary from biomarker to biomarker, and may include photometric, electrochemical, enzymatic, or immunogenic methods of determination using an antibody directed to the target biomarker.

The determination of the level of a selected metabolic biomarker such as glucose may be conducted photometrically, for example, using the hexokinase method, or electrochemically using glucose-oxidase-based methods. Glycated hemoglobin levels may also be determined chromatographically, photometrically, e.g. based on peroxidase activity of a hemoglobin/haptoglobin complex formed from the glycated hemoglobin, and by immunoassay, including ELISA and chemiluminescent immunoassay (CLIA).

The determination of creatinine levels may also be determined by absorbance/photometrically (e.g. using the Jaffe method for creatinine) or enzymatic (i.e., creatininase methods for creatinine measurement). Cystatin c levels may be determined photometrically, chromatographically, or by immunoassay, e.g. using a particle enhanced nephelometric immunoassay or latex enhanced immunoturbidimetric method.

Red cell distribution width is a measure of the range of variation of red blood cell volume that is reported as part of a standard complete blood count. RDW is calculated using the formula: RDW (%)=(Standard deviation of mean corpuscular volume (MCV)÷mean MCV)×100. RDW may be determined using an automated hematology analyzer. Elevated RDW is indicative of heart failure. RDW may be substituted with natriuretic peptides which may be detected by immunoassay, for example, including ELISA and chemiluminescent immunoassay.

Cardiac troponin levels, including troponin T and/or I, may be determined using immunoassay methodology (i.e., based on ELISA principles of sandwich or competitive immunoassays). These assays may be sensitive cardiac troponin (cTn) assays or highly sensitive cardiac troponin (hs-cTn) assays. Hs-cTn assays are herein defined as assays able to detect cTn in the single digit range of nanograms per litre, e.g., measurable concentrations less than 10 ng/L, with a coefficient of variation (CV) of <10% of the 99th percentile of cTn concentration in reference subjects (the recommended upper reference limit [URL]), and measurable concentrations of cardiac troponin in greater than 50% of a general population. Sensitive-cTn assays exhibit a CV of <20% at the 99th percentile URL, and measureable concentrations of cardiac troponin in a general population of less than 50%. Heart-specific fatty acid binding protein may also be detected using immunoassay.

The term "antibody" is used herein to refer to monoclonal or polyclonal antibodies, or antigen-binding fragments thereof, e.g. an antibody fragment that retains specific binding affinity for the target biomarker. Antibodies to target biomarkers are generally commercially available, for example, from Abnova, Origene, Novus Biologicals and Lifespan BioSciences, Inc. As one of skill in the art will appreciate, antibodies to the target biomarkers may also be raised using techniques conventional in the art. For example, antibodies may be made by injecting a host animal, e.g. a mouse or rabbit, with the antigen (target biomarker), and then isolating antibody from a biological sample taken from the host animal.

Different types of immunoassay may be used to determine expression level of target biomarkers, including indirect immunoassay in which the biomarker is non-specifically immobilized on a surface; sandwich immunoassay in which the biomarker is specifically immobilized on a surface by linkage to a capture antibody bound to the surface; competitive binding immunoassay in which a sample is first combined with a known quantity of biomarker antibody to bind biomarker in the sample, and then the sample is exposed to immobilized biomarker which competes with the sample to bind any unbound antibody. To the immobilized biomarker/antibody is added a detectably-labeled secondary antibody that detects the amount of immobilized primary antibody, thereby revealing the inverse of the amount of biomarker in the sample.

A preferred immunoassay for use to determine expression levels of protein biomarkers is an ELISA (Enzyme Linked ImmunoSorbent Assay) or Enzyme ImmunoAssay (EIA). To determine the level or concentration of the biomarker using ELISA, the biomarker to be analyzed is generally immobilized, for example, on a solid adherent support, such as a microtiter plate, polystyrene beads, nitrocellulose, cellulose acetate, glass fibers and other suitable porous polymers, which is pretreated with an appropriate ligand for the target biomarker, and then complexed with a specific reactant or ligand such as an antibody which is itself linked (either before or following formation of the complex) to an indicator, such as an enzyme. Detection may then be accomplished by incubating this enzyme-complex with a substrate for the enzyme that yields a detectable product. The indicator may be linked directly to the reactant (e.g. antibody) or may be linked via another entity, such as a secondary antibody that recognizes the first or primary antibody. Alternatively, the linker may be a protein such as streptavidin if the primary antibody is biotin-labeled. Examples of suitable enzymes for use as an indicator include, but are not limited to, horseradish peroxidase (HRP), alkaline phosphatase (AP), β-galactosidase, acetylcholinesterase and catalase. A large selection of substrates is available for performing the ELISA with these indicator enzymes. As one of skill in the art will appreciate, the substrate will vary with the enzyme utilized. Useful substrates also depend on the level of detection required and the detection instrumentation used, e.g. spectrophotometer, fluorometer or luminometer. Substrates for HRP include 3,3',5,5'-Tetramethylbenzidine (TMB), 3,3'-Diaminobenzidine (DAB) and 2,2'-azino-bis(3-ethylbenzothiazoline-6-sulphonic acid) (ABTS). Substrates for AP include para-Nitrophenylphosphates. Substrates for β-galactosidase include β-galactosides; the substrate for acetylcholinesterase is acetylcholine, and the substrate for catalase is hydrogen peroxide.

Following biomarker determinations, a laboratory score is allotted to each biomarker based on the concentration or level of that biomarker. For the metabolic biomarker, a determination of a concentration that is greater than a normal level, i.e. greater than the upper limit of the biomarker in a healthy individual, e.g. a non-diabetic individual, yields a score of 1. A level below this concentration yields a score of 0. For glucose, a concentration which is greater than the guideline recommended cutoff for glucose (e.g. >5.5 mmol/L for glucose as per the American Diabetes Association (ADA) guidelines), yields a score of 1. If HbA1c level is determined instead of glucose, a level of HbA1c of ≥6.5% from total hemoglobin in the system (e.g. the cutoff used by the ADA guidelines to diagnose diabetes using NGSP, or ≥48 mmol/mol using IFCC (International Federation of Clinical Chemistry) units) yields a score of 1. If a patient is known to be diabetic, then the metabolic biomarker determination may not be required and a score of 1 may be assigned.

For the biomarker related to heart function, a determination of the % of RDW which is greater than the prognostic RDW clinical cutoff (e.g. >13.3%) yields a score of 1. Alternatively, if natriuretic peptides are detected in place of RDW, then a determination of a level that is greater than the upper limit of the biomarker in a healthy individual (e.g. upper limit of normal) yields a score of 1 (i.e. BNP>35 pg/ml or NT-proBNP>125 pg/mL yield a score of 1). When % RDW is less than the cutoff, or natriuretic peptides levels are lower than the upper limit of normal, a score of 0 is allotted. If a patient has undergone a recent blood transfusion or has a history of heart failure, then determination of the heart function biomarker may not be required, and a score of 1 may be assigned.

For the biomarker related to renal (kidney) function, a determination of estimated glomerular filtration rate (eGFR) of less than the accepted normal value, e.g. <90 milliliters per minute per 1.73 m$^2$ (as determined by measuring creatinine or cystatin c, and calculated by CKD-EPI equation as described in Greenslade et al. *Ann Emerg Med.* 2013; 62:38-46) yields a score of 1. Otherwise, a score of 0 is allotted.

With respect to determination of a biomarker associated with cardiac injury, when cardiac troponin concentration is determined using a high-sensitivity assay (hs-cTn), then scores are allotted as follows:

a) if the hs-cTn concentration (first concentration) is greater than the cutoff of an ambulatory population at risk for future cardiovascular events, e.g. patients with established cardiovascular disease (secondary prevention) and patients at high risk of cardiovascular disease who have not yet established the disease (primary prevention), e.g. who have current symptoms of heart disease (such as have suffered a heart attack, suffer angina, or have received coronary revascularisation), those with symptoms of other arterial disease (such as stroke, transient ischaemic attack, or peripheral vascular disease), or the elderly, but less than the concentration where analytical variation has been reported (e.g. about 10 ng/L, thus, hs-cTn concentration range=cutoff to cutoff+10 ng/L), then a score of 1 is assigned. The cut-off may vary somewhat based on the high sensitivity cTn assay used, but will generally be less than 10 ng/L. Thus, in one embodiment, a score of 1 applies when the cTn concentration is less than about 20 ng/L.

In other embodiments, for example, using a hs-cTnI assay of Abbott Laboratories, a concentration between 4 ng/L to 14 ng/L yields a score of 1, for a hs-cTnI assay of Beckman Coulter, Inc., a concentration between 6 ng/L to 16 ng/L yields a score of 1, and for Roche Molecular Diagnostics' hs-cTnT assay, a concentration between 8 ng/L to 18 ng/L yields a score of 1;

b) if the hs-cTn concentration is greater than the first concentration in (a) but below the upper limit of normal (ULN) of a general population (e.g. the general population refers to all individuals without reference to any specific characteristic, comprising individuals of various ages and wellness), then a score of 2 is assigned. The cut-off may vary somewhat based on the high sensitivity cTn assay used. For example, using a hs-cTnI assay of Abbott Laboratories, a concentration between 15 ng/L to 30 ng/L yields a score of 2, for a hs-cTnI assay of Beckman Coulter, Inc., a concentration between 17 ng/L to 40 ng/L yields a score of 2, and for Roche Molecular Diagnostics' hs-cTnT assay, a concentration between 19 ng/L to 30 ng/L yields a score of 2;

c) if the hs-cTn concentration is greater than the upper limit of normal of a general population, then a score of 3 is assigned. The cut-off may vary somewhat based on the high sensitivity cTn assay used. For example, using a hs-cTnI assay of Abbott Laboratories, a concentration of greater than 30 ng/L yields a score of 3, for a hs-cTnI assay of Beckman Coulter, Inc., a concentration of greater than 40 ng/L yields a score of 3, and for Roche Molecular Diagnostics' hs-cTnT assay, a concentration of greater than 30 ng/L yields a score of 3.

When cardiac troponin concentration is determined using a sensitive assay (s-cTn), then scores are allotted as follows. For cardiac troponin I (cTnI), determination of a concentration of less than 0.01 ug/L yields a score of 0; determination of a concentration of 0.01 ug/L yields a score of 1; determination of a concentration of 0.02-0.03 ug/L yields a score of 2, and determination of a concentration of greater than 0.03 ug/L yields a score of 3. For cardiac troponin T (cTnT), determination of a concentration of less than 20 ng/L yields a score of 0; determination of a concentration of 20-30 ng/L yields a score of 1; determination of a concentration of 31-50 ng/L yields a score of 2, and determination of a concentration of greater than 50 ng/L yields a score of 3.

When heart-specific fatty acid binding protein (hFABP) is determined, scores are allotted as follows. If hFABP concentration is a first concentration greater than the cutoff that defines an ambulatory population at risk for future cardiovascular events, but less than the concentration where analytical variation has been reported, then a score of 1 is assigned. Levels that are less than this yield a score of 0. If hFABP concentration is greater than the first concentration but below the upper limit of normal (ULN) of a general population, then a score of 2 is assigned. If the hFABP concentration is greater than the upper limit of normal of the general population, then a score of 3 is assigned.

Thus, in one embodiment, the method of determining risk of an adverse cardiac event comprises the determination of the level of a metabolic marker (e.g. glucose/glycated hemoglobin), a biomarker indicative of heart function (e.g. RDW or natriuretic peptides) and a biomarker indicative of cardiac injury using a high sensitivity assay, e.g. hs-cTn. The score for each marker based on the levels of each is combined to yield a cumulative overall laboratory score. The maximum score is 5, and the minimum score is 0.

In another embodiment, the method of determining risk of an adverse cardiac event comprises the determination of the level of a metabolic marker (e.g. glucose/glycated hemoglobin), a biomarker indicative of renal failure (e.g. creatinine or cystatin c) and a biomarker indicative of cardiac injury using a high sensitivity assay, e.g. hs-cTn. The score for each marker based on the levels of each is combined to yield a cumulative overall laboratory score. The maximum score is 5, and the minimum score is 0.

In another embodiment, the method of determining risk of an adverse cardiac event comprises the determination of the level of a metabolic marker (e.g. glucose/glycated hemoglobin), a biomarker indicative of heart function (e.g. RDW or natriuretic peptides), a biomarker indicative of renal failure (e.g. creatinine or cystatin c) and a biomarker indicative of cardiac injury using a high sensitivity assay, e.g. hs-cTn. The score for each marker based on the levels of each is combined to yield a cumulative overall laboratory score. The maximum score is 6, and the minimum score is 0.

In another embodiment, the method of determining risk of an adverse cardiac event comprises the determination of the level of a metabolic marker (e.g. glucose/glycated hemoglobin), a biomarker indicative of heart function (e.g. RDW or natriuretic peptides), a biomarker indicative of renal failure (e.g. creatinine or cystatin c) and a biomarker indicative of cardiac injury using a sensitive assay, e.g. cTnI or cTnT. The score for each marker based on the levels of each is combined to yield a cumulative overall laboratory score. The maximum score is 6, and the minimum score is 0.

In another embodiment, the method of determining risk of an adverse cardiac event comprises the determination of the level of a metabolic marker (e.g. glucose/glycated hemoglobin), a biomarker indicative of renal failure (e.g. creatinine or cystatin c) and biomarkers indicative of cardiac injury using a sensitive assay, e.g. cTnI and cTnT. The score for each marker based on the levels of each is combined to yield a cumulative overall laboratory score. The maximum score is 8, and the minimum score is 0.

For laboratory scores close to 0, e.g. less than 2, less than 1 or 0, a patient is confirmed to be at low risk of an adverse cardiac event. For laboratory scores of greater than or equal to 4 wherein the maximum score is 5, or greater than or equal to 5 where the maximum score is 6, or greater than or equal to 7 wherein the maximum score is 8, the patient is confirmed to be at high risk of an adverse cardiac event, or death. The scores are indicative of the Liklihood Ratio (LR), i.e. the likelihood that a given test result would be expected in a patient that will experience an adverse cardiac event or death compared to the likelihood that that same result would be expected in a patient that will not experience an adverse cardiac event or death. Positive LR, i.e. the LR for positive results (a patient will experience an adverse cardiac event or death) is determined using the formula: sensitivity/1-specificity (of the method). Negative LR, i.e. the LR for negative results (a patient will not experience an adverse cardiac event or death) is determined using the formula: 1-sensitivity/specificity (of the method). Generally, a positive likelihood (LR+) ratio of greater than 1, preferably greater than 5, or greater than 10, indicates the test result is associated with an adverse cardiac event/death. A negative likelihood (LR−) ratio of less than 1, preferably less than 0.01, indicates that the result is associated with absence of an adverse cardiac event/death.

Following determination of a laboratory score for a given patient, the patient may then treated based on the laboratory score. For example, for patients confirmed to be at low risk of an adverse cardiac event or death (laboratory score of less than 2; LR− of less than 1), treatment is not required and the patient may be released from the hospital. For patients confirmed to be at high risk of an adverse cardiac event or death (laboratory score of greater than 4, 5 or ≥7; LR+ of greater than 1), the patient is administered an appropriate treatment, which may include one or more treatments selected from: administration of anticoagulants (e.g. warfarin, heparin, Dabigatran and low dose aspirin (75 mg daily)), thrombolytics (e.g. alteplase, reteplase, streptokinase, tenecteplase), nitroglycerin, antiplatelet drugs (e.g. clopidogrel, prasugrel or ticagrelor), beta blockers (e.g. propranolol, atenolol and bisoprolol), combined alpha and beta-blockers, calcium channel blockers (e.g. Amlodipine, Bepridil, Diltiazem, Felodipine, Nicardipine, Nifedipine, Nisoldipine, Verapamil), angiotensin-converting enzyme (ACE) inhibitors (e.g. Benazepril, Captopril, Enalapril, Fosinopril, Lisinopril, Moexipril, Perindopril, Quinapril, Ramipril, Trandolapril), angiotensin-receptor blockers (e.g. Candesartan, Eprosartan, Irbesartan, Losartan, Olmesartan, Telmisartan, Valsartan), angiotensin-receptor neprilysin inhibitors, cholesterol-lowering medications such as statins, vasodilators (e.g. hydralazine, hydralazine and isosorbide dinitrate), and/or diuretics (e.g. furosemide, bumetanide, torsemide, hydrochlorothiazide, metolazone, spironolactone); angioplasty and stenting; and coronary bypass surgery.

In another aspect of the invention, an article of manufacture or kit is provided that is useful to conduct the present method(s). The kit comprises one or more biomarker-specific reactant/reagents suitable for use to determine the level of biomarkers of the selected method in a biological sample from a mammal. For glucose, determination may be conducted using the hexokinase photometric method. Reagents may include: hexokinase, Glucose-6-phosphate dehydrogenase, adenosine triphosphate, nicotinamide adenine dinucleotide and/or (NAD). Creatinine determination may be conducted using the Jaffe method with the reagent, alkaline picrate, or using enzymatic reactions with enzyme reagents such as creatininase, creatine amidinohydrolase (creatinase) and sarcosine oxidase. For determination of glycated hemoglobin, as well as natriuretic peptides such as BNP and NT-proBNP, cystatin c, cardiac troponin I, cardiac troponin T and hFABP as biomarkers, determination may be conducted by immunoassay, utilizing antibodies (monoclonal or polyclonal) directed to the target biomarker(s). The kit may also include detectable markers which may be linked to the antibody or other component of the assay. Detectable markers may include radioactive, fluorescent, phosphorescent and luminescent (e.g. chemiluminescent or bioluminescent) compounds, dyes (e.g. leuco dyes), particles such as colloidal gold and enzyme indicators or labels. Additional reagents for inclusion in the kit may include distilled water, buffers, substrate for enzyme indicators and linkers as herein described.

The kit may additionally include instructions for conducting the method, as described herein, as well as instructions with respect to laboratory scoring based on the determined levels of biomarkers within a given sample. Further, the kit may include materials for conducting assays to determine levels of the biomarkers, such as test-tubes, cuvettes, other sampling containers and the like.

Embodiments of the invention are described by reference to the following specific examples, which is not to be construed as limiting.

Example 1

For a period of 5 weeks within Hamilton Health Sciences, ED nurses collected blood samples from patients (n=100, convenient sampling) being evaluated for acute coronary syndrome (ACS). Nurses collected blood at ED presentation: one blood sample for clinical measurements for cardiac troponin T (cTnT), complete blood count (CBC; which includes RDW) and glucose and another blood sample (serum separator tube—SST; gold top) for measurement of other cardiac biomarkers. A serum SST tube was used, as this is the preferred tube for many biomarkers; and allowed the serum specimens to be processed by the medical laboratory assistants without compromising the integrity of the sample (this type of specimen is preferred if testing is delayed). Following processing by the medical laboratory assistants, the separated serum specimens were transported to the Clinical Research and Clinical Trials Laboratory (CRCTL) at the Hamilton General Hospital for storage (below −80° C.).

An aliquot from the ED presentation sample (n=100) was thawed (8 months after collection) and measured using the following immunoassays (analyte/platform/company): 1) high-sensitivity cardiac troponin I (hs-cTnI/Access II instrument/Beckman Coulter) and 2) high-sensitivity cardiac troponin T (hs-cTnT/Elecsys 2010 instrument/Roche Diagnostics). The laboratory score (L5HF algorithm) was determined for hs-cTnI and hs-cTnT separately.

Briefly, the laboratory score was calculated as follows:
1. If the concentration of glucose was >5.5 mmol/L, then a score of 1 was assigned;
2. If red cell distribution width (RDW) was >13.3%, then a score of 1 was assigned; and
3. If a high-sensitivity cardiac troponin (hs-cTn) concentration was:
   a) greater than (>) the cutoff that defines an ambulatory population at risk for future cardiovascular events but less than the concentration where analytical variation has been reported (e.g., hs-cTn concentration range=cutoff to cutoff+10 ng/L), then a score of 1 was assigned, (e.g. for Beckman measurements of hs-cTnI, a concentration between 6 ng/L to 16 ng/L; for Roche measurements of hs-cTnT, a concentration between 8 ng/L to 18 ng/L).
   b) greater than (>) concentration (a) but below the upper limit of normal of a reference population then a score of 2 was assigned (e.g. for Beckman measurements, an hs-cTnI concentration between 17 ng/L to 40 ng/L; for Roche measurements, an hs-cTnT concentration between 19 ng/L to 30 ng/L);
   c) greater than (>) the upper limit of normal of a reference population then a score of 3 was assigned (e.g. for Beckman measurements, an hs-cTnI concentration >40 ng/L; for Roche measurements, an hs-cTnT concentration >30 ng/L).

Biomarker levels not within the ranges indicated above were given a score of zero. The sum of the scores from 1 to 3 above was obtained to determine the overall score (maximum score is 5, minimum score is 0) for hs-cTnI and hs-cTnT, separately.

Each patient was contacted up to 72 hours after their ED presentation to determine if a serious cardiac outcome, e.g. PCI, CABG, refractory ischemic symptoms, heart failure, myocardial infarction, stroke, cardiac arrest, or death, occurred within this timeframe. These outcomes were adjudicated by an emergency physician blinded to the exploratory biomarkers tested in the study population.

Results

There were 14 individuals from the 100 patients that experienced a serious cardiac outcome (+ Feature) within the first 72 hours. A laboratory score of 0 in the presentation sample determined either with the hs-cTnI or hs-cTnT assay yielded a likelihood ratio (LR) of 0 for an acute cardiovascular event (i.e. patients could be ruled-out). A laboratory score of 5 yielded the highest LR for a serious cardiac outcome within the first 72 hours (see TABLE 1 for laboratory score using hs-cTnI and TABLE 2 for laboratory score using hs-cTnT).

TABLE 1

Laboratory score determination using hs-cTnI assay (Beckman)

| Lab Score | +Feature | −Feature | Likelihood Ratio | 95% CI (Koopman) |
|---|---|---|---|---|
| 0 | 0 | 5 | 0 | 0 to 4.077487 |
| 1 | 0 | 19 | 0 | 0 to 1.005021 |
| 2 | 4 | 20 | 1.228571 | 0.471874 to 2.696732 |
| 3 | 1 | 31 | 0.198157 | 0.034793 to 0.906138 |
| 4 | 5 | 9 | 3.412698 | 1.30257 to 8.063795 |
| 5 | 4 | 2 | 12.285714 | 2.775149 to 52.796373 |

TABLE 2

Laboratory Score using hs-cTnT assay (Roche)

| Lab Score | +Feature | −Feature | Likelihood Ratio | 95% CI (Koopman) |
|---|---|---|---|---|
| 0 | 0 | 6 | 0 | 0 to 3.361013 |
| 1 | 2 | 22 | 0.558442 | 0.150915 to 1.696226 |
| 2 | 1 | 18 | 0.34127 | 0.058975 to 1.61906 |
| 3 | 3 | 21 | 0.877551 | 0.294353 to 2.175058 |
| 4 | 3 | 10 | 1.842857 | 0.576192 to 5.132779 |
| 5 | 5 | 9 | 3.412698 | 1.30257 to 8.063795 |

Example 2

Briefly, this was an all-comer ED population that consisted of all consecutive ED patients from two EDs over a period of 3 months who had glucose, RDW, and Abbott Laboratories hs-cTnI measurements (i2000 analyzer) available at presentation (n=4313). The outcome for this prospective observational study was hospital death.

In this Example, the laboratory score (L5HF algorithm) was determined in the same manner as in Example 1. Cardiac troponin was measured using an immunoassay by Abbott Laboratories. Briefly, the laboratory score was calculated as follows:
1. If glucose was >5.5 mmol/L then a score of 1 was assigned
2. If red cell distribution width (RDW) >13.3% then a score of 1 was assigned
3. If a high-sensitivity cardiac troponin (hs-cTn) concentration was:
a) greater than (>) the cutoff that defines an ambulatory population at risk for future cardiovascular events but less than the concentration where analytical variation has been reported (e.g. hs-cTn concentration range=cutoff to cutoff+10 ng/L), then a score of 1 was assigned (e.g. for Abbott hs-cTnI measurements, a concentration between 4 ng/L to 14 ng/L);
b) greater than (>) the concentration of (a) but below the upper limit of normal of a reference population, then a score of 2 was assigned (e.g. for Abbott hs-cTnI measurements, a concentration between 15 ng/L to 30 ng/L); or
c) greater than (>) the upper limit of normal of a reference population, then a score of 3 was assigned (e.g. for Abbott hs-cTnI measurements, a concentration of >30 ng/L).

The sum of the scores from 1 to 3 above was obtained to determine the overall score (maximum score is 5, minimum score is 0).

Also, as previously done in this population, the following was performed to assess LR for hospital death as described in Shout et al. *Clin Biochem* 2015; 48:282-7. Specifically, a dual panel testing was conducted in which Abbott hs-cTnI measurement <4 ng/L and glucose <5.6 mmol/L was a negative panel result, and either hs-cTnI or glucose concentration above these cutoffs (hs-cTnI >=4 or glucose>=5.6) yielded a positive result. A limit of detection (LoD) analysis was also conducted where the LoD was defined as <1 ng/L for a negative result, with >=1 ng/L defined as a positive result.

Results

There were 214 hospital deaths from the 4313 patients. The laboratory score of 0 in the presentation sample yielded a LR of 0 (no patients died with a score of 0) (see Table 3A), whereas both the dual testing (see Table 4) and LoD test (see Table 5) missed a patient. Combining laboratory scores of 0 & 1 produced a LR of 0.019 (95% CI: 0.003-0.108), lower than that of either the Dual Testing or LoD (see Table 3B). While combining laboratory scores of 4 & 5 yielded a significantly higher LR of 2.7 (95% CI: 2.4-3.0) as compared to dual testing (LR=1.12; 95% CI: 1.10-1.14) or LoD testing (LR=1.05; 95% CI: 1.03-1.06) (see Table 3B).

TABLE 3

Laboratory Score and Liklihood Ratio using Abbott hs-cTnI assay

| Lab Score | +Feature | −Feature | Likelihood Ratio | 95% CI (Koopman) |
|---|---|---|---|---|
| A) Likelihood Ratios for each laboratory score ||||| 
| 0 | 0 | 248 | 0 | 0 to 0.291536 |
| 1 | 1 | 735 | 0.02606 | 0.004599 to 0.145069 |
| 2 | 26 | 1128 | 0.441498 | 0.305255 to 0.627535 |
| 3 | 47 | 984 | 0.914886 | 0.701709 to 1.17283 |
| 4 | 57 | 562 | 1.942686 | 1.525054 to 2.436129 |
| 5 | 83 | 442 | 3.59683 | 2.95537 to 4.318031 |
| B) Likelihood Ratios for grouped laboratory scores ||||| 
| 0&1 | 1 | 983 | 0.019485 | 0.00344 to 0.108441 |
| 2&3 | 73 | 2112 | 0.662054 | 0.544007 to 0.79189 |
| 4&5 | 140 | 1004 | 2.670905 | 2.373192 to 2.965946 |

TABLE 4

Likelihood ratios using Abbott Dual Test (Glucose > 5.5 or hsTnI > 4 is positive)

| Dual Test | +Feature | −Feature | Likelihood Ratio | 95% CI (Koopman) |
|---|---|---|---|---|
| negative | 1 | 464 | 0.041281 | 0.007282 to 0.22994 |
| positive | 213 | 3635 | 1.122378 | 1.097257 to 1.136853 |

TABLE 5

Likelihood ratios using Abbott hs-cTnI LoD test (hs-cTnI concentration >= LoD is positive)

| [hs-cTnI] | +Feature | −Feature | Likelihood Ratio | 95% CI (Koopman) |
|---|---|---|---|---|
| <LoD | 1 | 208 | 0.092088 | 0.016213 to 0.51401 |
| >=LoD | 213 | 3891 | 1.048534 | 1.025681 to 1.058207 |

Example 3

Briefly, this study was based on an all-corner population that consisted of all consecutive ED patients from 2 EDs over a period of the first 2 months after clinically reporting hs-cTnI. The study population consisted of ED patients using only the first result of glucose, RDW, and Abbott Laboratories hs-cTnI measurements (i2000 analyzer) who also had an ED discharge home or hospital admission recorded (n=4444). The primary outcome for this prospective observational study was whether patients were eventually discharged from the ED or admitted as well as the length of stay in the ED with respect to different laboratory scores.

The laboratory score (L5HF algorithm) was determined in the same manner as in Example 2.

Results

There were 25 ED deaths in the population with all 25 having a laboratory score of 1 or higher (average laboratory score of 4). Those patients that were discharged home with a laboratory score of 0 in the earliest sample had a significantly shorter ED length of stay (median=5.6 hours) as compared to those with a score of 1 (median=6.0 hours); score of 2 (median=6.2 hours); score of 3 (median=6.8 hours); score of 4 (median=7.5 hours); or score of 5 (median=9.1 hours) ($p<0.05$, by Kruskal-Wallis: all pairwise comparisons by Conover-Inman).

Therefore, the lower the laboratory score, the higher the likelihood that patients would be discharged home (e.g., a laboratory score of 0 yielded a 95% upper confidence limit exceeding 10) with a laboratory score of 5 indicating a group of high risk patients that might not be discharged home (e.g., a laboratory score of 5 yielded a 95% lower confidence limit of 0.10) (see TABLE 6).

TABLE 6

Laboratory Score using Abbott hs-cTnI test clinically assessing the Likelihood ratios in ED patients that were discharged home or admitted to hospital

| Lab Score | Home | Admit | Likelihood Ratio | 95% CI (Koopman) |
|---|---|---|---|---|
| 0 | 230 | 30 | 7.5189 | 5.1785 to 10.931964 |
| 1 | 634 | 185 | 3.360975 | 2.886821 to 3.917328 |
| 2 | 712 | 466 | 1.498449 | 1.355143 to 1.65773 |
| 3 | 465 | 618 | 0.737925 | 0.664373 to 0.819366 |
| 4 | 131 | 452 | 0.284237 | 0.2361 to 0.341836 |
| 5 | 59 | 437 | 0.132409 | 0.101564 to 0.172388 |

Example 4

In this study adults presenting to the ED with symptoms of and investigated for acute coronary syndrome (ACS) were enrolled. Patients were excluded if they met any of the following exclusion criteria prior to cTnI testing: death, ST-elevation myocardial infarction (STEMI) and serious ventricular cardiac dysrhythmia or they had experienced one of the following conditions within the last month: cardiac surgery/manipulation, STEMI or NSTEMI (non-ST-elevation myocardial infarction); diagnosis of pulmonary embolus; malignancy; sepsis; or who were previously enrolled or transferred from another primary care facility. Patients were included in the analysis if they had presentation cTnI, glucose, hs-cTnI, hs-cTnT, eGFR and RDW values. The primary outcome was MI or all cause death at 30 days after presentation.

The laboratory score (L5HF algorithm) was determined in the same manner as in Examples 1 and 2.

The L5HF algorithm score consists of the following 3 tests (1 cardiac injury, 1 metabolic, and 1 heart function/hematology test used in patients with heart conditions) with the following values assigned to determine the overall score:

1. If glucose concentration (measurement via Hexokinase method or another method with acceptable agreement to this method) is >5.5 mmol/L, then assign a score of 1;
2. If red cell distribution width (RDW) (reported as RDW-CV=1SD/MCV×100 to yield a %, calculated from Beckman Coulter LH750 or another method with acceptable agreement) is >13.3% then assign a score of 1;
3. If a high-sensitivity cardiac troponin (hs-cTn) concentration is:
   a) Greater than (>) the cutoff that defines an ambulatory population at risk for future cardiovascular event but less than the concentration where analytical variation has been reported (e.g., hs-Tn concentration range=cutoff to cutoff+10 ng/L), then assign a score of 1 (e.g., for Abbott hs-cTnI measurements, concentration was between 4 ng/L to 14 ng/L; for Roche hs-cTnT measurements, concentration was between 8 ng/L to 18 ng/L);
   b) Greater than (>) concentration (a) but below the upper limit of normal of a reference population then assign a score of 2 (e.g., for Abbott hs-cTnI measurements, concentration was between 15 ng/L to 30 ng/L; for Roche hs-cTnT measurements, concentration was between 19 ng/L to 30 ng/L); or
   c) Is greater than the upper limit of normal of a reference population than assign a score of 3 (e.g., for Abbott hs-cTnI measurement, concentration was >30 ng/L; and for Roche hs-cTnT measurements, concentration was >30 ng/L).

Sum scores from 1 to 3 above to determine the overall score (maximum score is 5, minimum score is 0). Laboratory scores closer to 0 (e.g. less than 2) represent low risk patients that may be ruled out for a cardiac event, whereas laboratory scores closer to 5 (e.g. 4 or greater) represent high risk patients and would be ruled-in for further medical treatment and management.

The laboratory score was also was also determined using the following 3 tests (1 cardiac injury, 1 metabolic, and 1 renal test (e.g. the L5HR algorithm) as follows:

1. If glucose concentration (measurement via Hexokinase method or another method with acceptable agreement to this method) is >5.5 mmol/L then assign a score of 1
2. If estimated glomerular filtration rate (eGFR) (obtained by measuring creatinine and used in an equation such as CKD-EPI [chronic kidney disease epidemiologic collaboration equation] to derive the eGFR) is <90 milliliters per minute per 1.73 m$^2$ then assign a score of 1
3. If a high-sensitivity cardiac troponin (hs-cTn) concentration is:
   a) Greater than (>) the cutoff that defines an ambulatory population at risk for future cardiovascular event but less than the concentration where analytical variation has been reported (e.g., hs-Tn concentration range=cutoff to cutoff+10 ng/L), then assign a score of 1 (e.g., for Abbott hs-cTnI measurements, concentration was between 4 ng/L to 14 ng/L; for Roche hs-cTnT measurements, concentration was between 8 ng/L to 18 ng/L);
b) Greater than (>) concentration (a) but below the upper limit of normal of a general reference population then assign a score of 2 (e.g., for Abbott hs-cTnI measurements, concentration was between 15 ng/L to 30 ng/L; for Roche hs-cTnT measurements, concentration was between 19 ng/L to 30 ng/L); or
c) Is greater than the upper limit of normal of a general reference population than assign a score of 3 (e.g., for Abbott hs-cTnI measurement, concentration was >30 ng/L; and for Roche hs-cTnT measurements, concentration was >30 ng/L).

Sum scores from each test to determine the overall laboratory score (maximum score is 5, minimum score is 0). Laboratory scores closer to 0 (e.g. less than 2) represent low risk patients that may be ruled out for a cardiac event whereas laboratory scores closer to 5 (e.g. 4 or greater) represent high risk patients and would be ruled-in for further medical treatment and management.

The laboratory score was also determined using the following tests, e.g. determination of cardiac injury, 1 metabolic, 1 renal test and 1 heart function/hematology (e.g. the L6HHR algorithm) as follows:
1. If glucose concentration (measurement via Hexokinase method or another method with acceptable agreement to this method) is >5.5 mmol/L then assign a score of 1;
2. If red cell distribution width (RDW) (reported as RDW-CV=1SD/MCV×100 to yield a %, calculated from Beckman Coulter LH750 or another method with acceptable agreement) is >13.3% then assign a score of 1;
3. If estimated glomerular filtration rate (eGFR) (obtained by measuring creatinine and used in an equation such as CKD-EPI [chronic kidney disease epidemiologic collaboration equation] to derive the eGFR) is <90 milliliters per minute per 1.73 m² then assign a score of 1
4. If a high-sensitivity cardiac troponin (hs-cTn) concentration is as described above, then assign a score of 1, 2 or 3.

Sum scores from 1 to 4 above to determine the overall score (maximum score is 6, minimum score is 0). Laboratory scores closer to 0, e.g. less than 2, represent low risk patients that may be ruled out for a cardiac event, whereas laboratory scores closer to 6, e.g. 5 or more, represent high risk patients and would be ruled-in for further medical treatment and management.

The laboratory score was also determined using the following tests: 1 cardiac injury, 1 metabolic, 1 renal and 1 heart function/hematology test used in patients with heart conditions (L6SHR algorithm) as follows:
1. If glucose concentration (measurement via Hexokinase method or another method with acceptable agreement to this method) is >5.5 mmol/L then assign a score of 1;
2. If red cell distribution width (RDW) (reported as RDW-CV=1SD/MCV×100 to yield a %, calculated from Beckman Coulter LH750 or another method with acceptable agreement) is >13.3% then assign a score of 1;
3. If estimated glomerular filtration rate (eGFR) (obtained by measuring creatinine and used in an equation such as CKD-EPI [chronic kidney disease epidemiologic collaboration equation] to derive the eGFR) is <90 milliliters per minute per 1.73 m² then assign a score of 1;
4. If a sensitive cardiac troponin I (cTnI) concentration is:
a) Greater than (>) than the limit of detection (e.g., cTnI is measurable) then assign a score of 1 (e.g., using Abbott cTnI measurements the limit of detection is 0.01 ug/L (as <0.01 ug/L is undetectable and below the limit of detection);
b) Greater than (>) concentration (a) but below the upper limit of normal of a reference population then assign a score of 2 (e.g., using Abbott cTnI measurement, the concentration is between 0.02 ug/L to 0.03 ug/L);
c) Is greater than the upper limit of normal of a reference population than assign a score of 3 (e.g., using Abbott cTnI measurement, the concentration >0.03 ug/L.

Sum scores from 1 to 4 above to determine the overall score (maximum score is 6, minimum score is 0). Laboratory scores closer to 0, e.g. less than 2, represent low risk patients that may be ruled out for a cardiac event whereas laboratory scores closer to 6, e.g. 5 or more, represent high risk patients and would be ruled-in for further medical treatment and management.

The laboratory score was also determined using the following tests: 1 cardiac troponin I, 1 cardiac troponin T, 1 metabolic and 1 renal test (Labscore 8 algorithm) as follows:
1. If glucose concentration (measurement via Hexokinase method or another method with acceptable agreement to this method) is >5.5 mmol/L then assign a score of 1;
2. If estimated glomerular filtration rate (eGFR) (obtained by measuring creatinine and used in an equation such as CKD-EPI [chronic kidney disease epidemiologic collaboration equation] to derive the eGFR) is <90 milliliters per minute per 1.73 m² then assign a score of 1;
3. If cardiac troponin I concentration using a sensitive assay is as described above, then assign a score of 1, 2 or 3, as applicable.
4. If the concentration of cardiac troponin T using a sensitive assay is greater than or equal to 20 to 30 ng/L, assign a score of 1; if cardiac troponin T concentration is greater than 20 to 30 ng/L and below the upper limit of normal of a reference population, assign a score of 2; and if the cardiac troponin T concentration is greater than the upper limit of a reference population, assign a score of 3.

Sum scores from 1 to 4 above to determine the overall score (maximum score is 8, minimum score is 0). Laboratory scores closer to 0, e.g. 1 or less, represent low risk patients that may be ruled out for a cardiac event whereas laboratory scores closer to 8, e.g. 7 or greater, represent high risk patients and would be ruled-in for further medical treatment and management.

Thus, for each of the L5HF, L5HR, L6HHR, and L6SHR algorithms, a score <2 indicate a patient is at low risk that may be ruled out for a cardiac event, while a score >4 for L5HF and L5HR algorithms, or >5 for L6HHR and L6SHR algorithms, indicate a patient at high risk that would be ruled-in for further medical treatment and management. For the Labscore 8 algorithm, rule-out (low risk patient) was a score <1 and rule-in (high risk patient) was a score ≥7. The sensitivity, specificity, positive predictive value (PPV), and negative predictive value (NPV) was determined for all 5 algorithms using these cutoffs.

Results

There were 1095 patients who were evaluated by all 5 algorithms. The NPV and sensitivity were approximately 99% indicating that these algorithms can rule-out patients at presentation for MI or death within the next 30 days. The specificity and PPV were also high suggesting that these algorithms can also rule-in patients at ED presentation. TABLE 7 shows the diagnostic performance of all 5 algorithms (L6HHR, L6SHR, Labscore 8, L5HF, and L5HR) for ruling-out/in at ED presentation for 30 day MI or death in 1095 patients who present to the ED with symptoms suggestive of acute coronary syndrome.

TABLE 7

| Test | Liklihood Ratio (LR) | Sensitivity | Specificity | Positive predictive value | Negative predictive value |
| --- | --- | --- | --- | --- | --- |
| Rule-out | Negative LR | | | | |
| L6HHR with hsTnI as the assay Labscore <2 | 0.00 | 1.000 | 0.177 | 0.183 | 1.000 |
| L6SHR with cTnI as the assay Labscore <2 | 0.05 | 0.988 | 0.232 | 0.191 | 0.991 |
| Labscore 8 point Labscore <1 | 0.00 | 1.000 | 0.121 | 0.173 | 1.000 |
| L5HF with hsTnI as the assay Labscore <2 | 0.04 | 0.988 | 0.299 | 0.206 | 0.993 |
| L5HR with hsTnI as the assay Labscore <2 | 0.04 | 0.988 | 0.308 | 0.208 | 0.993 |
| L6HHR with hsTnT as the assay Labscore <2 | 0.03 | 0.994 | 0.177 | 0.182 | 0.994 |
| L5HF with hsTnT as the assay Labscore <2 | 0.02 | 0.994 | 0.283 | 0.203 | 0.996 |
| L5HR with hsTnT Labscore <2 | 0.04 | 0.988 | 0.294 | 0.205 | 0.993 |
| Rule-in | Positive LR | | | | |
| L6HHR with hsTnI as the assay Labscore >5 | 11.21 | 0.400 | 0.964 | 0.673 | 0.897 |
| L6SHR with cTnI as the assay Labscore >5 | 12.14 | 0.341 | 0.972 | 0.690 | 0.889 |
| Labscore 8 point Labscore >6 | 10.42 | 0.529 | 0.949 | 0.657 | 0.916 |
| L5HF with hsTnI as the assay Labscore >4 | 11.64 | 0.453 | 0.961 | 0.681 | 0.905 |
| L5HR with hsTnI as the assay Labscore >4 | 10.88 | 0.459 | 0.958 | 0.667 | 0.906 |
| L6HHR with hsTnT as the assay Labscore >5 | 5.37 | 0.435 | 0.919 | 0.497 | 0.899 |
| L5HF with hsTnT as the assay Labscore >4 | 5.86 | 0.494 | 0.916 | 0.519 | 0.908 |
| L5HR with hsTnT Labscore >4 | 5.25 | 0.476 | 0.909 | 0.491 | 0.904 | cardiovascular event or death (likelihood ratio=0, sensitivity=100% for laboratory score >0). This has not previously been possible using prior determinations of parameters such as high-sensitivity cardiac troponin limit of detection, either alone or in combination with glucose.

REFERENCES

1. Babuin L, Jaffe A S, Troponin: the biomarker of choice for the detection of cardiac injury. CMAJ 2005; 173:1191-1202.

DISCUSSION

Described are methods useful to determine risk in a patient of a cardiac event. The method includes determining levels of various biomarkers in a patient to yield a cumulative laboratory score. Scores close to 0 identify patients at low risk for an adverse cardiac event or death, who can be discharged after their initial blood work from the ED (thereby decreasing ED length of stay). The present methods are also useful to identify patients at high risk/high likelihood for an acute cardiovascular event or death. The determination of both low and high risks patients leads to the appropriate treatments/care/management to each patient, including care/treatment to the acute (e.g., ED setting), and non-acute (ambulatory or community) populations, as well as to patients at risk for cardiac injury.

The present study data indicates that a laboratory score of 0 can rule-out patients in the ED at presentation for an acute 2. Thygesen K, Alpert J S, White H D. Joint ESC/ACCF/AHA/WHF Task Force for the Redefinition of Myocardial Infarction. Universal definition of myocardial infarction. J Am Coll Cardiol. 2007; 50:2173-2195.
3. Kavsak P A, Allen L C, Apple F S, et al. Cardiac troponin testing in the acute care setting: Ordering, reporting, and high sensitivity assays—An update from the Canadian society of Clinical Chemists (CSCC). Clin Biochem 2011; 44:1273-77.
4. Thygesen K, Alpert J S, Jaffe A S, et al. Third universal definition of myocardial infarction. Circulation. 2012; 126(16):2020-35
5. Kavsak P A, Xu L, Yusuf S, McQueen M J. High-sensitivity cardiac troponin I measurement for risk stratification in a stable high-risk population. Clin Chem 2011; 57:1146-53.
6. Omland T, Pfeffer M A, Solomon S D, et al. Prognostic value of cardiac troponin I measured with a highly sensitive assay in patients with stable coronary artery disease. J Am Coll Cardiol 2013; 61:1240-9.
7. McQueen M J, Kavsak P A, Xu L, Shestakovska O, Yusuf S. Predicting myocardial infarction and other serious cardiac outcomes using high-sensitivity cardiac troponin T in a high-risk stable population. Clin Biochem 2013; 46:5-9.
8. Shortt C, Phan K, Hill S A, Worster A, Kavsak P A. An approach to rule-out an acute cardiovascular event for death in emergency department patients using outcome-based cutoffs for high-sensitivity cardiac troponin assays and glucose. Clin Biochem 2015; 48:282-7.
9. Felker G M, Allen L A, Pocock S J., et al. Red cell distribution width as a novel prognostic marker in heart failure. J Am Coll Cardiol 2007; 50:40-7.
10. Kavsak P A, Beattie J, Pickersgill R, Ford L, Caruso N, Clark L. A practical approach for the validation and clinical implementation of a high sensitivity cardiac troponin I assay across a North American city. Practical Laboratory Medicine 2015; 1:28-34.
11. Kavsak P A, Hill S A, Bhanich Supapol W, Devereaux P J, Worster A. Biomarkers for predicting serious cardiac outcomes at 72 hours in patients presenting early after chest pain onset with symptoms of acute coronary syndromes. Clin Chem 2012; 58:298-302.
12. Lippi G, Pavesi F, Bardi M, Pipitone S. Lack of harmonization of red blood cell distribution width (RDW). Evaluation of four hematological analyzers. Clin Biochem 2014; 47:1100-1103.
13. Patel K V, Semba R D, Ferrucci L, et al. Red cell distribution width and mortality in older adults: a meta-analysis. J Gerontal A Biol Sci Med Sci 2010; 65:258-265.
14. Greenslade J H, Cullen L, Kalinowski L, et al. Examining renal impairment as a risk factor for acute coronary syndrome: a prospective observational study. Ann Emerg Med. 2013; 62:38-46.
15. Shortt C, Ma J, Clayton N, Sherbino J, Whitlock R, Pare G, et al. Rule-in and rule-out of myocardial infarction using cardiac troponin and glycemic biomarkers in patients with symptoms suggestive of acute coronary syndrome (submitted to Clin Chem 2016).
16. Ponikowski P, Voors A A, Anker S D, et al. 2016 ESC Guidelines for the diagnosis and treatment of acute and chronic heart failure. European Heart Journal 2016; 37, 2129-2200.
17. Inker L A, Schmid C H, Tighiouart H, et al. Estimating Glomerular Filtration Rate from Serum Creatinine and Cystatin C. N Engl J Med 2012; 367:20-9
18. Apple F S. Counterpoint: Standardization of cardiac troponin I assays will not occur in my lifetime. Clin Chem 2012; 58:169-71.

We claim:

1. A method of identifying and treating a mammal at risk of an adverse cardiovascular event or death, wherein the mammal is not an ST-elevation myocardial infarction patient and the adverse cardiovascular event is selected from myocardial infarction, cardiac ischemia, heart failure, percutaneous coronary intervention (PCI) and coronary artery bypass graft (CABG)), said method comprises the steps of:
   i) detecting in a biological sample obtained from the mammal on presentation of symptoms of acute coronary syndrome, glucose at a concentration greater than 5.5 mmol/L and allotting a score of 1;
   ii) detecting in the biological sample obtained from the mammal on presentation of symptoms of acute coronary syndrome the level of a renal function biomarker selected from creatinine or cystatin c and allotting a score of 1 when the estimated glomerular filtration rate (eGFR) which is based on the level of the renal function biomarker is less than the normal level of eGFR;
   iii) detecting in the biological sample obtained from the mammal on presentation of symptoms of acute coronary syndrome the level of at least one biomarker of cardiac injury selected from cardiac troponin T (cTnT) and cardiac troponin I (cTnI) using a high sensitivity assay or a sensitivity assay and allotting a score of 1 if the level is greater than the level of an ambulatory population at risk for future cardiovascular events but less than the level at which analytical variation occurs, allotting a score of 2 if the level is greater than the level at which analytical variation occurs and less than the upper limit of normal of a general population, and allotting a score of 3 if the level is greater than the upper limit of normal of the general population;
   iv) generating a total laboratory score based on the sum of the scores for each of the biomarkers of i), ii) and iii), and identifying mammals at risk of an adverse cardiac event or death having a laboratory score of greater than 4, wherein the method exhibits a negative likelihood ratio of less than 1 with a sensitivity of about 99%, and a positive likelihood ratio of at least 5 with a specificity of at least about 90%; and
   v) administering a treatment to said mammals, wherein the treatment is selected from the group consisting of: administration of an anticoagulant, a thrombolytic, nitroglycerin, an antiplatelet drug, a beta blocker, an alpha and beta-blocker combination, a calcium channel blocker, an angiotensin-converting enzyme (ACE) inhibitor, an angiotensin-receptor blocker, an angiotensin-receptor neprilysin inhibitor, a cholesterol-lowering medication, a vasodilator, and/or a diuretic; angioplasty and stenting; and coronary bypass surgery.

2. The method of claim 1, wherein a score of 1 is allotted when the eGFR is less than 90 milliliters per minute per 1.73 m$^2$.

3. The method of claim 1, wherein a level of a heart function biomarker selected from red cell distribution width (RDW) and a natriuretic peptide is additionally determined, and a laboratory score of greater than 5 indicates a risk of an adverse cardiac event in the mammal.

4. The method of claim 3, wherein a score of 1 is allotted when the level of RDW as the heart function biomarker is greater than 13.3%, when the level of brain natriuretic peptide (BNP) as the natriuretic peptide is greater than 35 pg/ml or the level of amino-terminal pro-brain natriuretic peptide (NT-proBNP) as the natriuretic peptide is greater than 125 pg/mL.

5. The method of claim 1, wherein the biological sample is blood, serum, plasma, urine, and cerebrospinal fluid.

6. The method of claim 1, wherein when the cardiac injury biomarker is cardiac troponin T, determination of a concentration of 8-18 ng/L yields a score of 1, determination of a concentration of 19-30 ng/L yields a score of 2, and determination of a concentration of greater than 30 ng/L yields a score of 3.

7. The method of claim 1, wherein when the cardiac injury biomarker is cardiac troponin I, determination of a cTnI concentration of 4-14 ng/L yields a score of 1, determination of a concentration of 15-30 ng/L yields a score of 2, and determination of a concentration of greater than 30 ng/L yields a score of 3.

8. The method of claim 1, wherein the level of cardiac troponin T and cardiac troponin I as the biomarkers of cardiac injury are determined; and wherein a laboratory score of greater than or equal to 7 indicates a risk of an adverse cardiac event in the mammal.

9. The method of claim 8, wherein:
 i) a score of 1 is allotted when the eGFR is less than 90 milliliters per minute per 1.73 $m^2$;
 ii) for the cardiac injury biomarker troponin I, determination of a concentration of less than 0.01 ug/L yields a score of 0, determination of a concentration of 0.01 ug/L yields a score of 1, determination of a concentration of 0.02-0.03 ug/L yields a score of 2, and determination of a concentration of greater than 0.03 ug/L yields a score of 3; and
 iii) for the cardiac injury biomarker troponin T, determination of a concentration of less than 20 ng/L yields a score of 0, determination of a concentration of 20-30 ng/L yields a score of 1, determination of a concentration of 31-50 ng/L yields a score of 2, and determination of a concentration of greater than 50 ng/L yields a score of 3.

10. The method of claim 1, wherein the cardiac troponin I or cardiac troponin T is determined using a high sensitivity assay.

11. The method of claim 1, wherein the cardiac injury biomarker is cardiac troponin I determined using a sensitive assay.

12. The method of claim 1, wherein the cardiac injury biomarkers are cTnI and cTnT determined using a sensitive assay.

* * * * *